US008579947B2

(12) United States Patent
Wu

(10) Patent No.: US 8,579,947 B2
(45) Date of Patent: Nov. 12, 2013

(54) POLYPOROUS HOLLOW BONE SCREW

(76) Inventor: Yangguan Wu, Millburn, NJ (US)

( * ) Notice: Subject to any disclaimer, the term of this patent is extended or adjusted under 35 U.S.C. 154(b) by 454 days.

(21) Appl. No.: 12/807,785

(22) Filed: Sep. 14, 2010

(65) Prior Publication Data

US 2011/0093020 A1 Apr. 21, 2011

Related U.S. Application Data

(60) Provisional application No. 61/276,499, filed on Sep. 14, 2009.

(51) Int. Cl.
*A61B 17/86* (2006.01)

(52) U.S. Cl.
USPC ........... 606/301; 606/300; 606/302; 606/305; 606/306; 606/307; 606/308; 606/314; 606/317; 606/318; 606/319

(58) Field of Classification Search
None
See application file for complete search history.

(56) References Cited

U.S. PATENT DOCUMENTS

| | | | | |
|---|---|---|---|---|
| 6,086,589 | A * | 7/2000 | Kuslich et al. | 606/247 |
| 7,708,738 | B2 * | 5/2010 | Fourcault et al. | 606/67 |
| 8,317,799 | B2 * | 11/2012 | Schon et al. | 606/92 |
| 2005/0015061 | A1 * | 1/2005 | Sweeney | 604/264 |
| 2007/0161985 | A1 * | 7/2007 | Demakas et al. | 606/61 |
| 2010/0042215 | A1 * | 2/2010 | Stalcup et al. | 623/16.11 |

* cited by examiner

*Primary Examiner* — Elizabeth C Kemmerer
(74) *Attorney, Agent, or Firm* — Richard C. Litman

(57) ABSTRACT

Present invention depicts a poly-porous (micropore) hollow screws as diffusion chamber filled with core matrix for targeted delivery of growth factors and bone marrow stem cells. The screws comprise at least two parts: the distal part of the screw consists of the tip of the screw made of poly porous material and hollow inside proximally. It has threaded navel attached to the threaded nipple of the distal part of the proximal screw which has the screw head and is made of the solid material of the same kind. The screw head had hexagonal recess targeted for screw driver insertion. Assembly of screw created a chamber in the middle of the screw. The chamber is filled with core matrix consisting of gelatin nano-particles pre-impregnated with BMPs (BMP2/BMP7 for bone or BMP12 for tendon, ligament) and fibrin sealants or Chitosan dispersed with bone marrow stem cells and/or other growth factors. Bioactive protein core material is prepared during the surgery and filled the chamber of the screw by the surgeon. Fibrin sealants or Chitosan will polymerize to form a gel to hold the growth factors and stem cell in place. The screw can be used as the lag screw or other function to provide mechanical fixation in variety of condition. Once the screw implanted in the human body, the fibrin sealant or Chitosin/gelatin nano-particles are gradually degraded and slowly release growth factors and stem cells via micropores of screw to facilitate the bone healing and regeneration. The gelatin nanoparticles and fibril sealant/or Chitosan matrix also serve as the scaffold and platform for bone in-growth to the screw or alternatively, the stem cell inside of screw can regenerate new bone, providing the biological fixation. At the mean time as the bone regenerate and/or in growth, mechanical strength of the screw increased.

15 Claims, 5 Drawing Sheets

POLYPOROUS HOLLOW BONE SCREW

FIELD OF INVENTION

The present invention related to new type of screws that possess significant mechanical strength, yet, can slowly, sustained release fair amount of growth factors and stem cells to facilitate the tissue healing. The designed screw also encourages new bone in-growth/regeneration into the screw providing biological fixation. Possible application of the present invention is also defined.

BACKGROUND OF THE INVENTION

Bone is a naturally regenerative tissue possessing the capacity of healing from injury by recapitulating the embryonic skeletal developmental process. However, an estimated 5-10% of fractures fail to recover properly and proceed to delayed union or nonunion due to mechanical instability and/or poor biology (1). The mechanical problem is the one relatively easy one to be solved by external or internal fixation, but the biological issue remains a significant challenge (1). There are few fractures had tendency to undergo process of nonunion due to their unique anatomy. These include femur neck, scaphoid, talus neck, and Jone's fractures.

Femur neck fracture is one of the most common fractures treated surgically in orthopedic surgery. It comprises more than 50% of the hip fractures which is estimated to exceed 500,000 in United States by year 2041 as the population aging (2-34). Surgical fixation of the femur neck fracture is extremely challenging especially when fracture presents in elderly and fracture displaced. Due to poor bone quality and healing power in the elderly, higher rate of fixation failure including mal-union, nonunion and AVN had been reported in the literature in this group which causes high re-operating rate and increasing of the total cost (5, 6). Thus, hemiarthroplasty has been advocated by some surgeon (7). Despite the increasing cost for internal fixation, interestingly, more patient choose internal fixation over hemiarthroplasty based on recent cost-benefit analysis using the willingness to pay technique (8).

Mainstay of current internal fixation of femur neck fracture consists of lag screws and DHS. Lag screw fixation is the most popular technique used for femur fracture in United States. Most surgeons use 3 cancellous screws in an inverted triangular orientation. The inferior screw is recommended to be placed close to the calcar and anterior and posterior superior screw should put close or within 3 mm of the cortex to ensure better purchase. The cannulated screws are used with assistance of guide wire for parallel placement which allows dynamic compression. Lag screw fixation has advantage of minimally invasive insertion, limited disruption of femur head blood supply and superior torsional stability (9). However, strength of lag screw fixation is dependent on the quality of bone on the lateral wall of the proximal femur. Severe osteoporosis in elderly compromise strength of bone in support the screw fixation or in the fracture with vertical fracture line which imposes larger deforming force on the screw surpassing the capacity of screw fixation leads to fixation failure (7).

The challenge of fixation of femur neck fracture is not only come from the poor quality of the bone in the elderly but also from the biology of bone healing. Bone healing is slower in elder patient per se due to senesces of stem cells. The situation worsen in femur neck fracture because the femur neck is enveloped by synovial fluid, thus no periosteal blood supply and fracture disrupting the intraosseous blood circulation to the proximal fragment. Thus, any means to facilitate re-vascularization and bone healing will help to win the battle for racing between loss of reduction and bone healing.

Scaphoid is divided into proximal and distal poles, a tubercle, and the waist. eighty percent of the scaphoid is covered with articular cartilage. The main vascular supply is derived from scaphoid branch of the radial artery entering the dorsal ridge and supply 70%-80% of the scaphoid, including the proximal pole. Scaphoid fracture is the most common carpal fracture. Fracture through the waist or proximal pole disrupted the blood circulation, thus like femur neck fracture, had high incident of delayed or nonunion. Thus, screw fixation is recommended to achieve stable fixation thus revascularization of the proximal pole. Recently, percutaneous technique is advocated to preserve the circulation during the surgery (Kenneth, J Koval ed Hand book of fractures).

Talus fracture is the second in frequency among all tarsal fractures. Similar to the femur neck and scaphoid, majority (70%) of the talus is covered by articular cartilage No muscles originate or insert into the talus. The vascular supply to the talus depend on facial structures to reach talus, thus, in Hawkins' 3-4 talus neck fracture, capsule is disrupted which result in osteonecrosis (Keneth Koval ed Hand book of fractures).

The metadiaphyseal region of the $5^{th}$ metatarsal is an area of circulatory watershed resulting in limited blood supply. Fracture that occur at the meta-diaphyseal junction about 1.5 to 2.5 cm distal to metatarsal base, are commonly called Jones fracture. Because the comprised blood supply in this area, the fracture is at risk of nonunion. Thus, screw fixation is recommended for athletes to minimize the possibility of nonunion and prolonged restriction from activity (Jay Lieberman AAOS comprehensive review).

Tendon and ligament injury is the common injury in the sport. Healing of the ligament and tendon to the bone tunneling after reconstruction is the slow process resulting in prolonged restriction activity for the athletes to return the games. Speeding up the healing would be significantly beneficial to the survivorship of the graft and the athlete career.

Burst fracture is the fracture compression and flexion injury to the spine lead to the crushed of the vertebrate. The fracture are involved both anterior and middle column of the spine and is considered unstable fracture. The treatment includes the posterior pedicle screw fixation and possible anterior spine fusion. Pedicle screw can efficiently reduce the fracture of the vertebrate body by ligament taxis in most of time. The anterior spine fusion is only necessary to increase strength and support to anterior middle column to release the strain of the pedicle screw so that the later would not fail before the fracture healed. Thus, any means to facilitate the fracture healing may eliminate the need of anterior fixation.

Taking together, the unique injuries described above call for a biological active fixation device that can provide the mechanical strength and had capacity to stimulation healing.

Bone morphogetic proteins (BMPs) are a class of the proteins belonging to TGF beta superfamily and exhibiting potent osteoinductive activity in vivo. BMPs initially identified by their ability to induce ectopic, endochondral bone formation (Urist, 1965). Since then, 18 members of the BMP family have been identified. Structure and characterization of these proteins had been reviewed in detailed in recent patent application. US patent No 20090169592 "Osteogeneic devices and method of use thereof for repair of endonchondral bone and osteochondral defect". BMPs can be isolated in relative pure form by processes described in U.S. Pat. No. 4,294,935, 1981 and U.S. Pat. No. 4,455,256, 1983. Recently, Recombinant human BMP2 and BMP7 is made available by technique described in U.S. Pat. No. 6,150,328, 2000 and U.S. Pat. No. 7,459,527, 2008. Both BMP2 and BMP7 are potent osteoinductive agents, BMP2 either alone or in combination of other graft materials had shown to heal some critical size bone defect or nonunions. BMP2 and BMP7 are currently commercially available and FDA approved for treatment of the lumbar spine fusion and nonunion of the tibia fractures. BMP12, unlike BMP 2 and BMP7, exhibit the potent potential for tendon and ligament regeneration. Although BMPs is able to induce osteogenesis, or tendon/ligament genesis, very high dose is required to achieve such effect if use alone. To efficiently delivery of BMPs and improve their bioavailability, finding a suitable carrier is the major focus of the current research.

Search for the appropriate carrier for delivery of the BMPs started as early as discovery of the methods to purify MMPs. U.S. Pat. No. 4,526,909 to Urist, 1985 disclosed to used polymethylmethacrylate as delivery system for BMPs however, this system proved not working. BMPs are hydrophilic whereas, PMMA is hydrophobic. Most of the BMP will be trapped inside of the PMMA except the outer surface which can release by a leaching mechanism. Furthermore, monomer of PMMA and heat generated by polymerization will denature the protein thus inactivate the osteoinductive active of the BMPs. U.S. Pat. No. 4,596,574 to Urist, 1986 disclosed to use a biodegradable porous ceramics including tricalcium phosphate as carrier to deliver BMPs, it turn out to be great idea, porous ceramic not only able to control drug release but also attract stem cell in-growth thus augment host tissue integration. Porous ceramic is still use in combination of the organic polymers for drug delivery (U.S. Pat. No. 6,949,251). U.S. Pat. No. 4,563,489 disclosed of methods using biodegradable organic polymer, polylactic acid polymer as carrier for delivery of BMPs. it was proposed to use biodegradable material to make implant such screws. The idea is attractive because feature of biodegradability eliminate the possibility of hardware removal, however, this is not feasible because toxic degradation product and lack of mechanical strength. Since the early effort, many new materials have been developed as carrier for BMP delivery. The materials can be classified into two categories organic or inorganic. Inorganic carrier further divided as biodegradable or un-degradable. Most of organic carriers are biodegradable which further divided into hydrophobic or hydrophilic. These materials are used alone or in combination to control the rate BMP release so that bone formation is balance with rate of the biodegradation of the implant without de mechanical strength. The use of these materials is fully elucidated in following US patents (U.S. Pat. Nos. 6,110,484, 6,949,251, 6,544,290, 7,049,348, 7,192, 604, 6,949,590). Of all materials tested, however, gelatin is still most promising carrier.

Gelatin is nature polymers derived from denature of type I collagen. Gelatin derived from bovine or porcine has been widely used in pharmaceutical industry as capsule materials and stabilizer, gelatin also used as implant such gel-foam to stop surgical bleeding and demonstrated non-toxic, excellent biocompatibility and biodegradability. More importantly, Both BMP2 and BMP7 bind to the gelatin derived from bone, thus, better retain BMPs in the carrier. Porous form of gelatin is easy accessed by water and stem cells thus serve better as a carrier for BMPs. Recently, FDA approved clinical application of the porous collagen film as a carrier for BMP to enhance spine fusion (BMP-2) or healing of bone defect in nonunion (Medscape today, Carriers for BMPs). US patent NO. 20080294085 to Stamps disclosed collagen sponge rolled biphased ceramic to treat the precollapsed oateonecrosis of the femur head.

With advanced of nanotechnology, gelatin has been used to form a nanoparticles, natotubes and nanofibers. Natoparticle refers to the particles with diameters ranging from 10 nm to 1000 nm. Using nanoparticles as drug delivery system confirms sustained drug delivery, and subcellular action, therefore, significantly enhances the bioavailabilty of the drug. Preparation of gelatin nanoparticles is very simple by two step dissolvation methods. Gelatin nanoparticles are also easy to be crosslinked and chemically modified. Therefore, it has immense potential to be used for as colloidal drug delivery system. Other advantages are: It is inexpensive and can be sterilized (Mohsen, 2008). Study of BMP2 gelatin nanoparticles demonstrated that gelatin nanoparticles stabilize BMP2 for sustained release for a prolonged period of time (6 weeks in vitro and in vivo (Kempen et al Biomaterial 2008). Recently, human recombinant gelatin (rHG) is available as a source for preparation of nanoparticles to decrease risk of mad cow disease and lower the antigenicity. hHG nanoparticles exhibited good biocompatibility and controlled release of FITC-BSA (Young, 2009). Gelatin nanoparticle also exhibits protective effect of basic FGF (Tsutomu, 2007). In present invention, we use gelatin nanoparticle as a carrier for MMPs.

Stem cells refer to the cell able to differentiate into variety of lineage, yet maintain the ability to self renew. Mesenchymal stem cells (MSCs) are the pluripotent or multipotent stem cells capable of differentiating into osteogenic, chondrogenic, adipogenic and other mesenchymal lineages in vitro. MSCs are no specific marker, thus laboratory defined MSCs remains debatable. It is consensus that MSCs does express CD90 and CD105 but not express CD34 and CD 45. This may help for isolation of the MSCs. MSCs existed in many tissues including, adipose, muscles, liver, blood, as well as barrows. Bone marrow is the one of the richest resource for stem cells, and the most frequent donor site for harvesting stem cells for clinical use. The stem cells isolated from bone marrow refer to bone marrow stem cells (BMSCs). BMSCs are osteogenic, implantation of human BMSCs with a carrier into a critical size of bone defect which usually undergoes nonunion healed completely with short amount of the time (U.S. Pat. No. 686,900 to Kadiyala, 2005). Both autologous and allogenic MSCs can be used for orthopaedic surgery, autologous cells are preferred because it is non-immunogenic, easily accessible, sufficient resources available (only need 60 ml v.s 1.5 liter for other purpose). Standard procedure for isolation and purification of the MSCs from bone marrow consists of several steps: collection of the bone marrow aspirates, separation of nucleated cells from red cell, and purification of MSCs from other nucleated cells, clone selection and characterization as it delineated in the U.S. Pat. No. 7,015,037 to Furcht at el, 2006. Purification of the MSCs stem cells takes a few weeks to months to complete which renders multiple procedure and inconvenience for clinical use. Multiple purification steps in an open system can raise the risk of infection. In addition, in vitro differentiation and mutation is also a concern. Thus, application purified MSCs appears less attractive (Marcus et al 2009).

Collection and application of the bone marrow aspirates for bone regeneration and repair is a well know arts for centuries. However, clinical outcome is not consistent. Recent studies have shown that the key to effective clinical outcomes using MSC therapy is to provide that sufficient number of the MSCs cells to the patient which repairs the bone or tissue defects. This refers to "Regenerative MSC Threshod" (Kadiyala, 2005). Bone marrow aspirates are usually collected from the iliac crest. It contains red blood cells, lymphocytes, granucytes, monocytes, fibroblasts, stem cells including bone stem cells which possess only very small percentage of all cell populations. Therefore in order to achieve Regenerative MSC Threshold, a method needs to enrich MSCs in the bone marrows aspirates, a process often referred as concentration. Ficoll gradient centrifugation is well known art for making bone marrow aspirate concentrates (BMAC). However, this is an open system required special equipment, and time consuming (need at least 45 to 1 hours), required appropriate trained personnel. U.S. Pat. No. 6,981,948 to Pellegrino 2006 disclosed a bone marrow aspiration system in which bone marrow aspirates allowed to pass through chamber containing graft substrates during the collection procedure. The cell retains in the graft material and ready for implantation. The attraction of this design is simple, quick, efficiency, and in the closed system. However, this system fails to separate the richest red blood cells from other cells. U.S. Pat. No. 424,973 to Augustus disclosed a 17.3% glucose gradient centrifuge for concentration of bone marrow aspirates which only need 10 minutes, however, like other gradient centrifuge methods, it is an open system and require special equipment. Recently, a new closed Harvest BMAC system can complete concentration in 10 to 15 minute and available in USA. Recently, Asian described an immuno-isolation to purify MSCs without culture results in 60 times increase in fibroblast CFU as compare those without purification. One aim of the present invention is to provide a clinical usable approach to further enrich MSCs.

In addition to the number of the MSCs, like BMPs, methods of delivery and retention of the MSCs in the site of action is also important for clinical application of MSCs osteogenesis. Many carriers have been tried for delivery of MSCs but most of them are lack of ability to retain MSCs. Thus majority of stem cell migrate away through the blood circulation after implantation decrease its bioavailability. Since MSCs is alive, It significantly limited the materials which can be used to encapsulate the cell in their matrices.

Carrier for stem cells is limited with respect of cell retention, most of the carriers are pre-casted, thus retention of the cell is a problem unless the carrier modified with special affinity molecule. e.g. RGD. In situ polymerized implant has advantage of cell retention, however, heat generation during polymerization and toxic monomers create hostile environment for live cell to survive. Thus, few polymers qualified as in situ polymerizing system for cell delivery (U.S. Pat. No. 6,110,484 to Sierra). Chitosan and fibril sealant are two of few candidates.

Chitosan is a biocompatible nature polymer developed as a delivery vehicle for the peptide (U.S. Pat. No. 2008213354 to Sung). It exhibits thermosensitive property in presence certain inorganic phosphate salts such as glycerol phosphate or tiacalcium phospate, the liquid chitosan solution transformed into a gel at clinically feasible time ranging from 2 to 10 minutes at 37° C. Chitosan have been used extensively for chondral cell transplantation (Marchand, 2009) Chitosan will serve as an alternative for delivery of MSCs In present invention.

Fibrin sealant as delivery system for drugs including growth factors and stem cells is a well known art in the field. Variety applications of fibrin sealant have been nearly exhausted in a world patent (WO/1996/040174, Supplement and un-supplemented tissue sealants, methods of their production and use). Fribrin sealants are two component tissue adhesive systems mimicking natural clot cascade. Two components of fibrin adhesives are stored in sterilized lyophilized powder. The components are reconstituted into liquid form by adding distilled water. As two component mixed together, they polymerized at the site of application into a relatively dense gel. Thrombin in combination of $Ca^{2+}$ catalyze polymeration of fibrinogen, converting the fibrinogen into fibril polymer. Further, thrombin and $Ca^{2+}$ activate coagulation factor XIII, which leads to covalent crosslinking of fibrin. The rate of proteolytic degradation of the fibrin polymer clot is decreased and mechanical stability is increased as a result of the covalent crosslinking of the polymer. Presence of fibronectin (U.S. Pat. No. 51,412 to Shane) and hyaluronic acid (U.S. Pat. No. 6,503,527 to whitmore) inhibit the proteolytic degradation, increase the fibril stability.

The fibrin polymer clot is porous with pore size range from 1 to 5 microns in mean diameter. It is too small to allow cell move freely. However, the micro-pore allows easy diffuse of nutrition, growth factor and hormone to maintain normal cellular activity and function. To move in the fibril matrices, cell has to secrete protease or stimulate the other cells such as macrophage to produce protease to degrade the fibril. Thus, fibrin polymer serves as a barrier for the stem cells till degradation of the fibrin polymer and/phagocytosis is complete.

Study using fibrin sealant as carrier for cell transplantation is a well known art. Several studies have used fibrin sealant to delivery chondrocytes to repair the chondrodefect in the knee. The resultant repair does not exhibit hypertrophy shown in cell transplant alone. The beauty of this art is that preparation is in liquid form after injection the fibrin polymerized in situ forming an ideal shape implant predetermined by the defect. Fibrin sealant also attempted to use as carrier for delivery of MSCs stem cell or BMPs to heal bony defect, interestingly, the bone growth in fibrin sealant group is not as robust as compare to other carrier such gelatin. However, fibrin sealant group does show more angiogenesis than other group (review articles). Fibrin sealant as carrier for angiogenesis growth factors exhibited potent agiogenesis potential in animal model and in vitro experiments (Andreas et al Molecular Medicine 2007 and US patent to Shane). Use of the fibrin sealants as carrier for stem cells use for osteogenesis is not fully explored ad is one aim of the present invention.

Bone screws are a basic part of modern internal fixation. They can be used independently, or, in particular types of implants, they can be used together with the implant. The common design of a screw consists of a tip, shaft, thread, and head. A round screw tip requires pretapping, whereas a fluted screw tip is self-tapping. The screw shaft is located between the head and the threaded portion of the screw. The screw thread is defined by its major or outside (thread diameter) and minor or root (shaft diameter) diameters, pitch, lead, and number of threads. The distance between adjacent threads is the pitch.

The 2 basic types of screws available for the variability of bone density are cortical and cancellous screws. Cortical screws are designed for compact diaphyseal bone, whereas cancellous screws are designed for the more trabecular metaphyseal bone. Cortical screws have a smaller major (thread) diameter, decreased pitch, and a shallower thread than cancellous screws. Cancellous screws typically have a larger major (thread) diameter and pitch and a greater difference between major and minor (shaft) diameters in comparison to cortical screws, providing more surface area for bone purchase. These screws are intended for use in metaphyseal fixation, where bone is softer.

A few new designs have made in screws to improve and expand their function in fracture fixation. Biodegradable screw is a very attractive design, since it eliminates possible hardware removal after fracture healing and potential to use it as target drug delivery. Extensive research has been focused in this area. Many drugs including BMPs and biodegradable materials have been tested and or proposed to form a drug delivery screws. Although the system has the capacity to carry significant amount of the drug, which able to sustain release for a long time, toxic reaction to the break down product and weak mechanic strength make the idea not feasible, except few condition where toxic reaction overweight the benefit of the treatment such as cancer (Brode, Integrascience).

Coating of a screw is another new development. In recent studies Mauni demonstrated that hydroxyl apetite (HA) coated screws improve fixation and outcomes in osteoporosis fracture (JOT 2009). Alex use Chitosan coated stainless steel screw to fix the contaminated fracture and demonstrated that gentamicin can be eluted from implant at detectable level for 96 hours. However, the drawback of this system is the dosage limitation during coating.

Porous material serve as a barrier to control the drug delivery is an ancient art for pharmaceutical industry. Author in 1990 have used hollowed polyporous hydroxyl apatite implant to control release of adriamycin, and observed a sustained release for over 45 days in vivo. Recent art of using porous material as out shell and degradable core to for drug delivery demonstrated zero order prolonged stable sustained release (Ca patent 2363902 to Fesrehaie). US Patent NO 2007161985 to Demakas et al disclosed a "porous screw" which has a channel inside had at least one pore on lateral wall, the pore is filled with PMMA and BMPs to allow bone structure to grow into the "porous screw". However, BMP release from the PMMA is limited. US patent 20090192552 disclosed a special screw with expansible sleeve to anchor the bone while a hollow core used for injection of bone cement to enforce the fixation. The above idea is quite interesting. However, they are not suitable for delivery of stem cells, the other important component for bone formation and scope of clinical application is not clearly defined except spine surgery. Since bioactive agents release from above invention is limited and diffuse through full length of the screw, they may help bone in-growth to the implant at sub-cellular level to create biological fixation. Thus, this screw may be suitable for position screw fixation.

Since sustained high local concentration is critical for osteoinductive activity of BMPs and stem cell. A hollowed poly-porous screw with define chamber filling with biodegradable protein core is used in present invention as a barrier for targeted delivery and controlled release of BMP and stem cell to the injury site to facilitate tissue healing. Targeted delivery achieved to by using this new screw for fixation as lag screw, interference screw, and pedicle screw.

SUMMARY OF THE INVENTION

A new type of screw created in present invention comprises two parts: anterior part of the screw consisting of screw tip and hollow core inside is made from poly-porous titanium or tetanlum with micropore size ranging from 200-500 micron. The micropores are engineered to be interconnected using the well known technology for the materials. The surface of the anterior part of screw can be no thread, partially threaded, or full threaded depended on the clinical application. The length of the anterior part of the screw is also variable according to clinical setting. Inside of proximal end consists threaded navel attached the threaded nipple of the proximal part of the screw. The proximal part of screws consists of a shaft and screw head or head less with a hexagonal recess for screw driver. Outside of the shaft can be threaded or no threaded according clinical application and length of shaft varied corresponding to length of distal part to center the hollow core to fracture site. Assembly of the screw creates a chamber serving as a reservoir for bioactive materials. The micropores in distal part of screw allow bioactive agents and cells to diffuse in and outside of chamber based on concentration gradient to the surrounding tissue.

The bioactive materials used in this invention comprises BMPs impregnated gelatin nanoparticles, partial purified autologous stem cells, and fibrin sealants.

rhBMP2 (Medtronic, Minneapolis) and rhBMP7 (Stryker, Mass) are chosen for bone healing in present invention because their safety and clinical efficiency approved by FDA. BMP12 chosen for tendon and ligament regeneration is prepared according to (U.S. Pat. No. 6,719,968). rHG is chosen to prepare gelatin nanoparticles since it is lack of immunogenicity and has no risk of mad cow disease. BMPs impregnated gelatin nanaparticles are prepared by adding BMPs prior second disolvation step in two desolvation methods. Genipin is used for crosslinking the nanoparticles to increase stability. BMP impregnated nanoparticles are lyophilized and sterilized with radiation for storage.

Autologous stem cells prepared with two simple steps intraoperatively in closed system: bone marrow aspirates concentration and immu-isolation. Bone marrow aspirates are collected intra-operatively from iliac crest, and concentrated with Harvest MBAC system available in USA. MBAC system consists of a desk top centrifuge can accommodate four dual chamber. The bone barrow aspirates loaded in the upper chamber, 10 minute centrifugation separates red cells which stay in top chamber and nucleated cells which decanted to the low chamber with plasma. The cell pallets are transferred to a sterilized flask containing serum free MSC culture medium mixed with sterilized anti CD105 antibody conjugated magnetic nanoparticles (In vitrogen) for 20 minutes at 37° C. The flask then placed in a magnetic holder and rolled gently for 5 minutes. CD105 positive stem cells will be pulled down onto the wall of the flask by magnetic field, the floating cells will be discarded. Partial purified CD 105 positive stem cells are released by brief treatment of trypsin. Activity of trypsin is terminated by adding serum containing medium. Stem cells are them collected by brief centrifuge.

Artiss Fibrin sealant (Baxter) is chosen because both components of fibrin sealant are derived from human source and phase 3 clinical trial show great safety. The product mimics the final stage of coagulation cascade. The product comes in two sterilized vials in lyophilized form. Part A contains fibrinogen, Part B contains thrombin. The product is reconstituted with distilled water provided in the kit. The BMPs impregnated gelatin nanoparticles and cell pallets will be re-suspended in part A liquid, part B is then added and mixed well. The mixture is then loaded to the screw chamber via a plastic adaptor. A reasonable force was applied to ensure the micro-pore has been completely filled with the bioactive materials. The chamber is sealed by assembly the screw. The fibrin sealant polymerized to form a gel.

Chitosan is a biocompatible nature polymer developed as a delivery vehicle for the peptide (U.S. Pat. No. 2008213354 to Sung). It exhibits thermosensitive property in presence certain inorganic phosphate salts such as glycerol phosphate or tiacalcium phospate, the liquid chitosan solution transformed into a gel at clinically feasible time ranging from 2 to 10 minutes at 37° C. Chitosan have been used extensively for chondral cell transplantation (Marchand, 2009). Chitosan can be used as an alternative to fibrin sealant. In this case the cells and BMPs impregnated gelatin nanoparticles will mixed with liquid form of the Chitosan and loaded to screw chamber. The screw is then inserted to into bone to fix the fracture. Chitosan then becomes a gel under the body temperature. One advantage of Chitosan is easy handling. The disadvantage is its safety as an implant has been reviewed by FDA.

Regardless Fibrin salant or Chitosan as a carrier, the resultant bioactive screw can then be utilized as a lag screw either alone or in combination of other fixation device to stabilize fracture.

The gel formed by fibrin sealant and Chitosan is a porous structure, once implanted in the body, it allows the diffusion of the nutrient but migration of the cell requires enzymatic degradation. Thus fibrin sealant or Chitosan matrices may serve as a barrier to prevent the stem cells quickly diffuse away into blood circulation. Gelatin nanoparticles retain BMPs and slowly release BMPs in proximity to stem cells in the paracellular fashion priming the stem cell to differentiate into osteogenic lineage. The BMPs primed stem cells can migrate out of screw through micropore to the fracture in response to the cytokine in the fracture site to help the bone healing via osteogenic process. The released BMP can also diffuse out the screw resulting high concentration locally at fracture site facilitate bone healing through osteo-induction. Furthermore, the stem cells in the screw can form bone in response to BMPs, alternatively, BMP can induce bone growth to the pore of the screw, resulting biological fixation. At mean time, mechanical strength of the screw will increase as bone growth in the screw.

Intracapsular fractures refer to the fracture in the bone covered by articular capsules. Healing of the intracapular fracture is always issues due to following reason: 1) No periosteal membrane, thus lack of blood supply from the outer cortexes and source of callus formation from periostium. 2) Joint fluid infiltrate the fracture site dilutes and or wash away the necessary cytokines, growth factures, and cellular components for bone healing. 3) Solo vascular supply is easily disrupted in displaced intracapsular fracture lead to delayed or nonunion. Example of intracapsular fractures included femur neck fracture, scaphoid fracture and talus fracture. Although, growth factors and stem cells is plausible for improve the fracture healing and revascularization, however, deliver of the bioactive agents is not possible with regular means due to accessibility. Using the present invention to fixation intracapsular fractures the BMP and stem cells can slowly release to the fracture site to help the fracture healing and prevent nonunion. In this special setting VEGF can also added to fibrin sealant/or Chitosan matrix to speed up revascularization. Similarly, bioactive screws may be used to heal the Jone's fractures.

Interference screw is the primary fixation methods for the reconstruction surgery for sport injury. Post-surgery rehabilitation is very lengthy take about 6 months to 1 year. Using bioactive interference screw (use BMP2, or BMP7 if bone to bone healing, use BMP12 if ligament or tendon to bone healing), the growth factors and stem cells can speed up the healing process. This may reduce the risk of the graft failure and encourage the athlete return to game earlier. The present invention can also serve as pedicle screw for bust fracture in the spine.

BRIEF DESCRIPTION OF THE FIGURES

FIG. 1 FIG. 1a. is an isomeric view of the new 7.3 mm cancellous screw. The crossline indicates the junction between the proximal and distal part of the screw. The proximal part is made of the solid material, whereas the distal part is made of the polyporous materials. The size of the shaft is 7.3. mm in diameter. The size of the screw head is 8.0 mm in diameter. The screw length is 90 mm with proximal part of 30 mm and distal part of 60 mm. The chamber in the distal part of the screw is 5.0 mm in diameter and spans the entire length of the distal screw. The tip is tapered. The length of the threaded part of the distal screw is 30 mm with a pitch of 1.25 mm and lead of 2.5 mm. FIG. 1b shows an explosion view of the proximal and distal part junction. The proximal threaded nipple is ready to mate to the distal thread naval. The thread in the junction part is counterclockwise so that when the screw advances it tightens the junction. FIG. 1c is the 3D section view shows a chamber forms after screw assembly. FIG. 1D is the front view shows the hexagonal recess for screw driver. FIG. 1e is the right side view showing the relative dimension of the screw head, shaft, and the tip FIG. 2 Screw designed for scaphoid fracture. Herbert screw is 2.0 mm, distal ¼ part from tip has cancellous thread with larger lead, small pitch and a hollow core diameter about 1 mm, The proximal end of the screw has cancellous thread about ⅕ of screw length with larger pitch, small lead. Middle of the shaft is smooth. The junction between distal and proximal is located in ⅔ from screw tip. Similar design can apply to talus fracture with larger diameter of 3.5 mm FIG. 3 Interference screw is taper shape with cancellous thread. The hollow part of the screw extends to distal ⅔ length of the screw. The solid part of the screw only serve as a cap and screw driver adaptor.

DETAILED DESCRIPTION OF THE INVENTION

Figure 1:
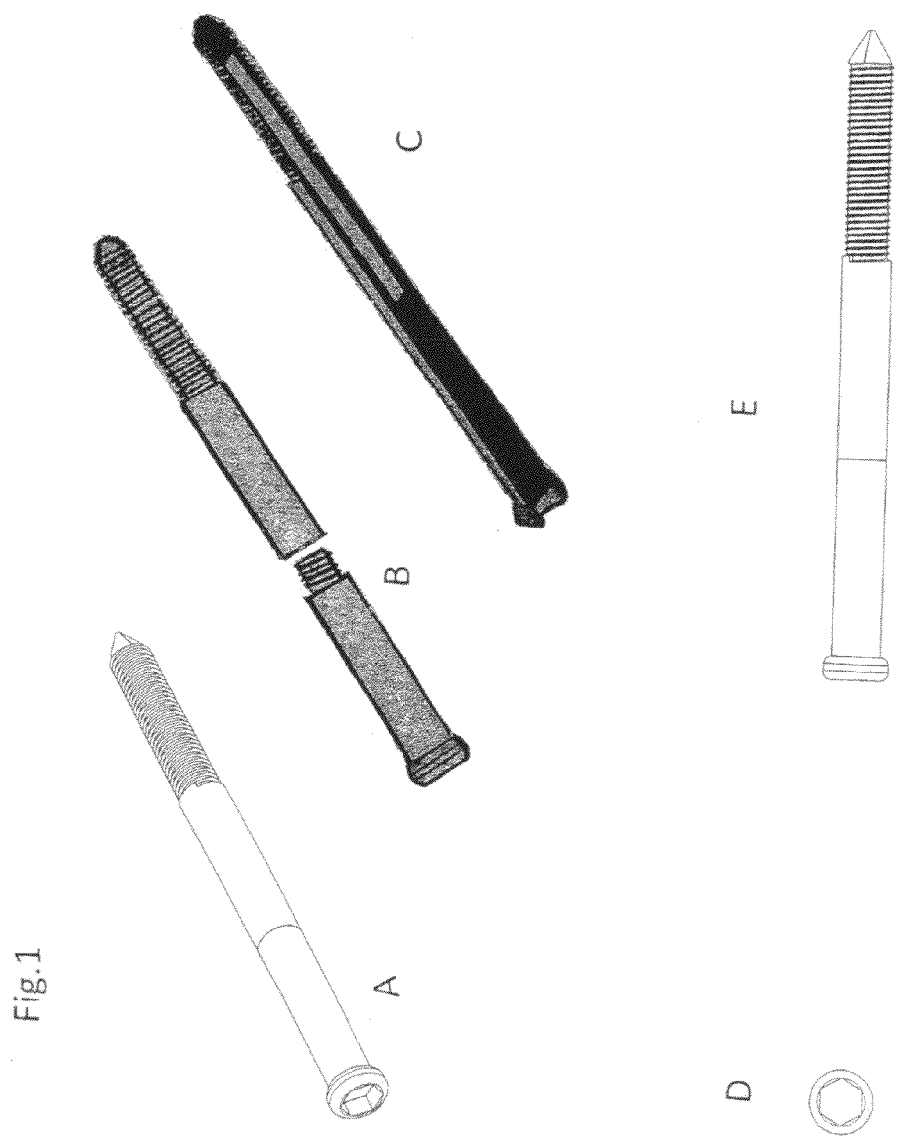

A new type of screw created in present invention consists of two major components: the poly-porous hollow screw and core matrix. The poly hollow screw functions as a fixation device also serves as reservoir, diffusion barrier and delivery tool to bring the growth factors and stem cell directly to the site of action; whereas core matrix function as carrier for growth factors and stem cells also serves as the platform for priming stem cell differentiation and scaffold for osteoinductive and osteogenic activity.

Poly-porous screw is made from tantalum, a composite of reticulated vitreous carbon foam and tantalum metal. The material is made by applying tantalum metal to a reticulated vitreous carbon foam construct in a chemical vapor infiltration process, which is a chemical vapor deposition (CVD).

The screw comprises two parts: anterior part of the screw consisting of screw tip and hollow core inside is made from poly-porous tetanlum with micropore size ranging from 200-500 micron. The micropores are engineered to be interconnected using the well known technology for the materials. The surface of the anterior part of screw can be no thread, partially threaded, or full threaded depended on the clinical application. The length of the anterior part of the screw is also variable according to clinical setting. Inside of proximal end consists threaded navel attached the threaded nipple of the proximal part of the screw. The proximal part of screws consists of a shaft and screw head or head less with a hexagonal recess for screw driver. Outside of the shaft can be threaded or no threaded according clinical application and length of shaft varied corresponding to length of distal part to center the hollow core to fracture site.

Assembly of the screw creates a chamber serving as a reservoir for bioactive materials. The micropores in distal part of screw allow bioactive agents and cells to diffuse in and outside of chamber based on concentration gradient to the surrounding tissue.

The core matrix used in this invention comprises BMPs impregnated gelatin nanoparticles, partial purified autologous stem cells dispersed in fibrin sealants or Chitosan matrix.

rhBMP2 (Medtronic, Minneapolis) and rhBMP7 (Stryker, Mass) are chosen for bone healing in present invention because their safety and clinical efficiency approved by FDA. BMP12 chosen for tendon and ligament regeneration is prepared according to (U.S. Pat. No. 6,719,968). rHG is chosen to prepare gelatin nanoparticles since it is lack of immunogenicity and has no risk of mad cow disease. BMPs impregnated gelatin nanaparticles are prepared by adding BMPs prior second disolvation step in two desolvation methods. Genipin is used for crosslinking the nanoparticles to increase stability. BMP impregnated nanoparticles are lyophilized and sterilized with radiation for storage. Briefly, 1.25 g of rHG was dissolved in 25 ml of water under heating and stir. 25 ml of ethano was added to the solution to separate the high molecular weight gelatin. The sediment was collected and redissolved with 100, 200, and 400 ml of water. Prior to the second desolvation step, 2.2-5 mg BMPs was dissolved in the 40 ml of gelatin for 3 hrs at 37 C. After incubation, various volume of ethanol containing genipin ranging from 57-62% were added. The final concentration of genipin was fixed at 0.05%. The BMP-gelatin nanoparticles were cross linked in 37 C water bath for 72 hrs, and then ethanol was evaporated by rotary evaporator. The nanoparticles were further purified and lyophilized for long term use.

Autologous stem cells prepared with two simple steps intra-operatively in closed system: bone marrow aspirates concentration and immu-isolation. Bone marrow aspirates are collected intra-operatively from iliac crest, and concentrated with Harvest MBAC system available in USA. MBAC system consists of a desk top centrifuge can accommodate four dual chamber. The bone barrow aspirates loaded in the upper chamber, 10 minute centrifugation separates red cells which stay in top chamber and nucleated cells which decanted to the low chamber with plasma. The cell pallets are transferred to a sterilized flask containing serum free MSC culture medium mixed with sterilized anti CD105 antibody conjugated magnetic nanoparticles (In vitrogen) for 20 minutes at 37° C. The flask then placed in a magnetic holder and rolled gently for 5 minutes. CD105 positive stem cells will be pulled down onto the wall of the flask by magnetic field, the floating cells will be discarded. Partial purified CD 105 positive stem cells are released by brief treatment of trypsin. Activity of trypsin is terminated by adding serum containing medium. Stem cells are them collected by brief centrifuge.

Artiss Fibrin sealant (Baxter) is chosen because both components of fibrin sealant are derived from human source and phase 3 clinical trial show great safety. The product mimics the final stage of coagulation cascade. The product comes in two sterilized vials in lyophilized form. Part A contains fibrinogen, Part B contains thrombin. The product is reconstituted with distilled water provided in the kit. The BMPs impregnated gelatin nanoparticles and cell pallets will be re-suspended in part A liquid, part B is then added and mixed well. The mixture is then loaded to the screw chamber via a plastic adaptor. A reasonable force was applied to ensure the micro-pore has been completely filled with the bioactive materials. The chamber is sealed by assembly the screw. The fibrin sealant polymerized to form a gel.

Chitosan is a biocompatible nature polymer developed as a delivery vehicle for the peptide (U.S. Pat. No. 2008213354, to Sung). It exhibits thermosensitive property in presence certain inorganic phosphate salts such as glycerol phosphate or tiacalcium phospate, the liquid chitosan solution transformed into a gel at clinically feasible time ranging from 2 to 10 minutes at 37° C. Chitosan have been used extensively for chondral cell transplantation (Marchand, 2009). Chitosan can be used as an alternative to fibrin sealant. In this case the cells and BMPs impregnated gelatin nanoparticles will mixed with liquid form of the Chitosan and loaded to screw chamber. The screw is then inserted to into bone to fix the fracture. Chitosan then becomes a gel under the body temperature. One advantage of Chitosan is easy handling. The disadvantage is its safety as an implant has been reviewed by FDA.

Regardless Fibrin salant or Chitosan as a carrier, the resultant bioactive screw can then be utilized as a lag screw, either alone or in combination of other fixation device to stabilize fracture.

The gel formed by fibrin sealant and Chitosan is a porous structure, once implanted in the body, it allows the diffusion of the nutrient but migration of cell requires enzymatic degradation. Thus fibrin sealant or Chitosan matrices may serve as a barrier to prevent the stem cells quickly diffuse away into blood circulation. Gelatin nanoparticles retain BMPs and slowly release BMPs in proximity to stem cells in the paracellular fashion priming the stem cell to differentiate into osteogenic lineage. The BMPs primed stem cells can migrate out of screw through micropore to the fracture in response to the cytokine in the fracture site to help the bone healing via osteogenic process. The released BMP can also diffuse out the screw resulting high concentration locally at fracture site facilitate bone healing through osteo-induction. Furthermore, the stem cells in the screw can form bone in response to BMPs, alternatively, BMP can induce bone growth to the pore of the screw, resulting biological fixation. At mean time, mechanical strength of the screw will increase as bone growth in the screw.

Significant advantage of use invented screw for fixation of the following clinical example.

Intracapsular fractures refer to the fracture in the bone covered by articular capsules. Healing of the intracapsular fracture is always issues due to following reason: 1) No periosteal membrane, thus lack of blood supply from the outer cortexes and source of callus formation from periostium. 2) Joint fluid infiltrate the fracture site dilutes and or wash away the necessary cytokines, growth factures, and cellular components for bone healing. 3) Solo vascular supply is easily disrupted in displaced intracapsular fracture lead to delayed or nonunion. Example of intracapsular fractures included femur neck fracture, scaphoid fracture and talus fracture. Although, growth factors and stem cells is plausible for improve the fracture healing and revascularization, however, deliver of the bioactive agents is not possible with regular means due to accessibility. Using the present invention to fixation intracapsular fractures the BMP and stem cells can slowly release to the fracture site to help the fracture healing and prevent nonunion. In this special setting VEGF can also added to fibrin sealant/or Chitosan matrix to speed up revascularization. Similarly, bioactive screws may be used to heal the Jone's fractures.

Example 1 femur neck fracture is one of common fracture treated by the orthopaedic surgeons. Fixation of the displaced femur neck fracture remains extremely challenging. In addition to the above mention healing disadvantage of the intracapsular fracture. Femur neck fracture has character of the high stress on the fracture site, poor quality of the bone and lower healing power due quiescence of the stem cells in aged individual. The designed screw as showed in FIG. 1 has larger diameter 7.3 to bear the high stress, long shaft smooth screw easy to cross the fracture side. The screw tip is round to avoid the cutting out. Partially cancellous thread allowed the fracture fragment sliding and impaction to improve chance of the healing and screw purchase in the distal fragment (FIG. 1). The core matrix for femur eck fracture includes BMPs, stem cells as well as VEGF to facilitate the re-vascularization and bone healing. On the other hand, BMP and stem cells in screw also encourage the bone in-growth to screw strengthening screw fixation. Three screw will be inserted in the reverse triangle to prevent the rotation instability and also increase the dose of the growth factor and stem cells delivery to the fracture side.

Example 2

Figure 5:
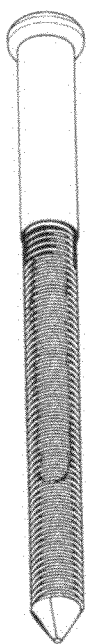
FIG. 5. Lag screw for Jones fracture. 3.5 mm partial threaded and porous material made of anterior ⅔ of the screw from the tip. The hollow core is located in the middle third.

Talus neck fracture is also intra-articular fracture usually resulted from high energy injury. Thus, fracture can occur in both the young and elderly. Since the talus is small. The force required to maintain the fracture from displacement is relatively small. Thus, 3.5 mm screw was chosen (FIG. 5). The screw is also partially threaded to provide the fragment compression. The cortical screw design may be used for young patient who had good bone quality. Cancellous screw is used for elder patient with poor bone quality. Similarly, Stem cell can be eliminated from core matrix for young patient because they have the good reserve of stem cell for rebusted osteoinductive activity. Similar construct can be used for Jone's fracture Example 3

Figure 2:
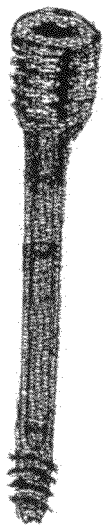

Scaphoid is very unique. Articular cartilage cover most of the surface the scaphoid. Thus, any screw prominent with damage joint. Thus, a Herbert screw design was used (FIG. 2). Since the scaphoid is small, 2.0 mm screw is recommended. Due to limitation of chamber volume, the stem cell will not used. Bt VEGF will used to improve vasculization.

Example 4

Figure 3:
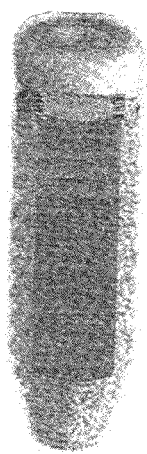

Interference screw is the primary fixation methods for the reconstruction surgery for sport injury. Post-surgery rehabilitation is very lengthy take about 6 months to 1 year. Graft failure due to using bioactive interference screw (use BMP2, or BMP7 if bone to bone healing, use BMP12 if ligament or tendon to bone healing), the growth factors and stem cells can speed up the healing process. This may reduce the risk of the graft failure and encourage the athlete return to game earlier. The interference screw is taper shape with cancellous thread. This would increase the pull out strength of graft. The delivery chamber spans entire screw increase the exposure of the graft and host to the growth factor and stem cell thus enhance the chance of their integrating (FIG. 3).

Example 5

Figure 4:
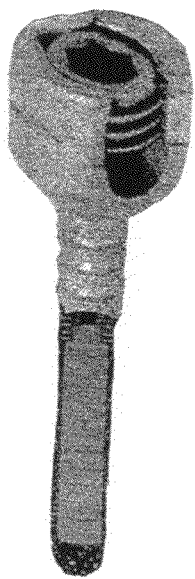
FIG. 4. Pedicle screw. screw shaft is screw peg design. Porous part is the peg about 2.5 mm-3.5 mm occupy ⅔ length of screw. Solid structure consists of the rest of screw.

Pedicle screw fixation if one of the major advancement in orthopaedic spine surgery. However, fixation failure occur frequently due to poor quality of the bone in aged patient. The invented embodiment is using the screw peg design (FIG. 4). The solid portion of the screw connected linker to the rod had the thread to inserted through pedicle which has better bone quality. The porous portion of the screw as extended to the vertebrate. Inside of the peg is hollow as delivery chamber. Peg design expands the available space for chamber without loss of the mechanical strength. Core matrix in the peg contains growth factors and stem cell, which able of release to the vertebrate to improve the bone quality. Furthermore the growth factor, stem cells also encourage screw and bone incorporated to form a biological fixation.

REFERENCE

1. Wozney, J M., Spine 2002, 27 S2-S8.
2. Paker, M. J. The management of intracapsular fractures of the proximal femur. JBJS 82(B):937-941, 2000.
3. Molton, L. J., II. Hip fracture: a world wide problem today and tomorrow. Bone S1-58, 1993
4. Papadimitropoulos E. A., Coyte, P. C., Josse, R. G., et al: Current and projected rates of hip fracture in Canada CMAJ. 157:1357-1363.
5. Bhandari, M., Devereaux, p. J., Swiontkowski, M. F., et al. internal fixation compared with arthroplasty for displaced fracture s of femur neck. A meta-analysis. JBJS 85-A: 1673-1681
6. Masson M, Parker M. J, Fleischer S: Internal fixation versus arthroplasty for intra-capsular proximal femur fractures in adults Cochrance Database Syst. Rev 2:CD001
7. Bhandari M, Devereaux, P. J., Tonetta, P. $3^{rd}$ et al: Operative management of displaced demur neck fractures in elderly patients. An international survey. JBJS. 87-A:2122-2130, 2005.
8. Alolabi, B., Bajammal, S., Shiravi, J., Karanicolas, P. J., Gani, A., Bhandari, M. Treatment of displaced femur neck fractures in the elderly: A cost-benefit analysis. J Orthop. Trauma 23(6): 442-446, 2009.
9. Bhandari, M., Tornetta, p., Hanson, B., Swiontkowski, M. F. Optimal interal fixation for femoral neck fractures: Multiple screw or sliding hip screws? J Orthop. Trauma. 23(6): 402-407, 2009.
10. Urbaniak, J. R. and E. J. Harvey Revascularization of the femual head in Osteonecrosis Journal of American Academy of Orthopaedic Surgeon 6(1):44, 1998.
11. Korompilias A. V, Lykissas, M. G., Beris, A. E., Urbaniak, J R. Soucacos, P. N. Vascularised fibular in the management of hemur head oseonecrosis: twenty years later JBJS 91(3B), 287-93, 2009.
12. Free Vascularized fibular transfer for femoral head osteonecrosis: donor and graft site motbidity JBJS 91(AM):1861-7, 2009.
13. Ramesh Kumar Sen at el. Management of avascular necrosis of femur head at precollapse stage. India J Orthop 2009; 43:6-16.

The invention claimed is:

1. A polyporous hollow bone screw which serves as a diffusion chamber, comprising:
    a hollow bone screw forming a hollow chamber, said hollow bone screw being filled with a biodegradable core matrix as a carrier for bioactive materials;
    the biodegradable core matrix being selected from the group consisting of gelatin nanoparticles, fibril sealant, and chitosan nanoparticles; and
    the bioactive materials being selected from the group consisting of growth factors and bone marrow stem cells.

2. The polyporous hollow bone screw according to claim 1, wherein said bone screw includes a distal part A and a proximal part B, wherein said distal part A is made of a porous material having interconnected pores ranging from 200-500 microns in diameter and a porosity of 40-50% and said proximal part B is titanium or tantalum.

3. The polyporous hollow bone screw according to claim 2, wherein said distal part A and said proximal part B are joined by an internal thread that is formed between a threaded nipple on the distal end of said proximal part B and a threaded navel on the proximal end of said distal part A;
- wherein said internal thread is threaded such that the junction is tightened when the screw is advanced; and
- wherein coupling of said distal part A and said proximal part B via said internal thread forms a hollow chamber for delivery of said bioactive materials.

4. The polyporous hollow bone screw according to claim 2, wherein said bone screw includes a screw tip that is tapered or fluke-shaped.

5. The polyporous hollow bone screw according to claim 2, wherein the outside of said distal part A comprises cortical or cancellous thread and outside of said proximal part B has no thread.

6. The polyporous hollow bone screw according to claim 5, wherein said distal part A has a distal section and a proximal section, the cortical or cancellous thread being disposed only on the distal section and no thread being disposed on the proximal section, thereby forming an unthreaded middle shaft between said distal part A and said proximal part B.

7. The polyporous hollow bone screw according to claim 6, wherein said middle shaft has the same diameter as the shaft of said proximal part B.

8. The polyporous hollow bone screw according to claim 1, wherein the internal diameter of said hollow chamber is about ⅓ to ⅔ the outer diameter of the screw.

9. The polyporous hollow bone screw according to claim 1, wherein the screw includes an enlarged screw head with a hexagonal recess at the proximal end of the screw head.

10. The polyporous hollow bone screw according to claim 1, wherein said biodegradable core matrix comprises gelatin nanoparticles pre-impregnated with a growth factor selected from the group consisting of BMP-2, BMP-7, and MMP-12.

11. The polyporous hollow bone screw according to claim 1, wherein said biodegradable core matrix comprises fibril sealant dispersed with: a) a growth factor selected from the group consisting of BMP-2, BMP-7, and MMP-12; and/or b) bone marrow stem cells.

12. The polyporous hollow bone screw according to claim 11, wherein said fibril sealant comprises pooled fibrinogen and thrombin, wherein when the fibrinogen and thrombin are mixed, said fibrinogen is converted to fibril monomers which spontaneously aggregate to form a fibril clot, and wherein the aggregate is cross-linked via Factor Xllla.

13. The polyporous hollow bone screw according to claim 1, wherein said biodegradable core matrix comprises chitosan nanoparticles dispersed with: a) a growth factor selected from the group consisting of BMP-2, BMP-7, and MMP-12; and/or b) bone marrow stem cells.

14. The polyporous hollow bone screw according to claim 13, wherein each of said chitosan nanoparticles comprises a first component comprising said bioactive materials, a second component of low molecule weight chitosan, and a third component comprising a negatively charged organic compound, wherein said second component dominates on a surface of said nanoparticle, and wherein said negatively charged organic compound is complexed with a substantial portion of said low molecular weight chitosan.

15. The polyporous hollow bone screw according to claim 1, further comprising VEGF.

\* \* \* \* \*